US010709483B2

(12) United States Patent
Voellmicke et al.

(10) Patent No.: US 10,709,483 B2
(45) Date of Patent: Jul. 14, 2020

(54) LAMINOPLASTY PLATES AND METHODS OF EXPANDING THE SPINAL CANAL

(71) Applicant: DEPUY SYNTHES PRODUCTS, INC., Raynham, MA (US)

(72) Inventors: John C. Voellmicke, Franklin, MA (US); Edward Zalenski, Lakeville, MA (US); Michael D. Sorrenti, Middleboro, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 263 days.

(21) Appl. No.: 15/726,750

(22) Filed: Oct. 6, 2017

(65) Prior Publication Data

US 2018/0042649 A1    Feb. 15, 2018

Related U.S. Application Data

(60) Continuation of application No. 14/986,780, filed on Jan. 4, 2016, now Pat. No. 9,795,420, which is a continuation of application No. 13/905,643, filed on May 30, 2013, now abandoned, which is a division of
(Continued)

(51) Int. Cl.
*A61B 17/70* (2006.01)
*A61B 17/00* (2006.01)

(52) U.S. Cl.
CPC ...... *A61B 17/7071* (2013.01); *A61B 17/7059* (2013.01); *A61B 2017/00004* (2013.01); *A61B 2017/00526* (2013.01)

(58) Field of Classification Search
CPC .................................................. A61B 17/7071
See application file for complete search history.

(56) References Cited

U.S. PATENT DOCUMENTS

| 4,972,949 A | 11/1990 | Peiffer |
| 5,085,660 A | 2/1992 | Lin |
| 5,133,735 A | 7/1992 | Slater |

(Continued)

FOREIGN PATENT DOCUMENTS

| EP | 0599640 | 8/1998 |
| WO | WO 1995011632 | 5/1995 |

(Continued)

OTHER PUBLICATIONS

U.S. Appl. No. 13/857,309, Zalenski et al., filed Apr. 5, 2013, now U.S. Pat. No. 8,926,616—Jan. 2015.
(Continued)

*Primary Examiner* — Olivia C Chang
(74) *Attorney, Agent, or Firm* — Sergio Chung

(57) ABSTRACT

A method of expanding the spinal canal of a vertebra including inserting a bone anchor into a first lamina of the vertebra, cutting completely through the first lamina to create a space in the first lamina, cutting partially through a second, contra-lateral of the vertebra to create a partial cut in the second lamina, engaging a first segment of a plate with the bone anchor, pivoting the bone anchor and the first lamina about the partial cut in the second lamina to increase the extent of the space in the first lamina, and connecting a second segment of the plate to a portion of the vertebra across the space from the first segment of the plate such that the plate spans the space and stabilizes the vertebra.

11 Claims, 7 Drawing Sheets

Related U.S. Application Data application No. 12/609,251, filed on Oct. 30, 2009, now Pat. No. 8,470,003.

(56) References Cited

U.S. PATENT DOCUMENTS

| | | |
|---|---|---|
| 5,133,736 A | 7/1992 | Bales |
| 5,141,519 A | 8/1992 | Smith |
| 5,147,360 A | 9/1992 | Dubousset |
| 5,147,378 A | 9/1992 | Markham |
| 5,152,778 A | 10/1992 | Bales |
| 5,152,780 A | 10/1992 | Honkanen |
| 5,176,702 A | 1/1993 | Bales |
| 5,192,298 A | 3/1993 | Smith |
| 5,199,566 A | 4/1993 | Oritz |
| 5,290,299 A | 3/1994 | Fain |
| 5,336,228 A | 8/1994 | Cholhan |
| 5,366,455 A | 11/1994 | Dove |
| 5,380,324 A | 1/1995 | Muller |
| 5,411,522 A | 5/1995 | Trott |
| 5,423,826 A | 6/1995 | Coates |
| 5,466,243 A | 11/1995 | Schmieding |
| 5,470,333 A | 11/1995 | Ray |
| 5,487,741 A | 1/1996 | Maruyama |
| 5,498,263 A | 3/1996 | DiNello |
| 5,501,683 A | 3/1996 | Trott |
| 5,507,747 A | 4/1996 | Yuan |
| 5,527,312 A | 6/1996 | Ray |
| 5,531,745 A | 7/1996 | Ray |
| 5,558,674 A | 9/1996 | Heggeness |
| 5,616,144 A | 4/1997 | Yapp |
| 5,637,112 A | 6/1997 | Moore |
| 5,704,936 A | 1/1998 | Mazel |
| 5,722,976 A | 3/1998 | Brown |
| 5,735,852 A | 4/1998 | Amrein |
| 5,735,899 A | 4/1998 | Schwartz |
| 5,746,743 A | 5/1998 | Greenberg |
| 5,830,231 A | 11/1998 | Geiges |
| 5,922,008 A | 7/1999 | Gimpelson |
| 5,951,557 A | 9/1999 | Luter |
| 5,961,530 A | 10/1999 | Moore |
| 5,993,449 A | 11/1999 | Schlapfer |
| 6,080,157 A | 6/2000 | Cathro |
| 6,136,002 A | 10/2000 | Shih |
| 6,273,253 B1 | 8/2001 | Forster |
| 6,287,307 B1 | 9/2001 | Abboudi |
| 6,325,625 B1 | 12/2001 | Meyer |
| 6,355,038 B1 | 3/2002 | Pisharodi |
| 6,440,135 B2 | 8/2002 | Orbay |
| 6,458,131 B1 | 10/2002 | Ray |
| 6,460,700 B2 | 10/2002 | Weisshaupt |
| 6,530,933 B1 | 3/2003 | Yeung |
| 6,572,617 B1 | 6/2003 | Senegas |
| 6,610,091 B1 | 8/2003 | Reiley |
| 6,626,909 B2 | 9/2003 | Chin |
| 6,626,916 B1 | 9/2003 | Yeung |
| 6,626,929 B1 | 9/2003 | Bannerman |
| 6,635,087 B2 | 10/2003 | Angelucci |
| 6,652,527 B2 | 11/2003 | Zucherman |
| 6,660,007 B2 | 12/2003 | Khanna |
| 6,663,654 B1 | 12/2003 | Husain |
| 6,669,697 B1 | 12/2003 | Pisharodi |
| 6,712,820 B2 | 3/2004 | Orbay |
| 6,719,795 B1 | 4/2004 | Cornwall |
| 6,767,351 B2 | 7/2004 | Orbay |
| 6,811,567 B2 | 11/2004 | Reiley |
| 6,880,699 B2 | 4/2005 | Gallagher |
| 6,974,478 B2 | 12/2005 | Reiley |
| 6,981,990 B2 | 1/2006 | Keller |
| 6,997,953 B2 | 2/2006 | Chung |
| 7,074,239 B1 | 7/2006 | Cornwall |
| 7,087,084 B2 | 8/2006 | Reiley |
| 7,090,676 B2 | 8/2006 | Huebner |
| 7,201,751 B2 | 4/2007 | Zucherman |
| 7,264,620 B2 | 9/2007 | Taylor |
| 7,320,689 B2 | 1/2008 | Keller |
| 7,344,537 B1 | 3/2008 | Mueller |
| 7,452,368 B2 | 11/2008 | Liberatore |
| 7,569,067 B2 | 8/2009 | Keller |
| 7,625,376 B2 | 12/2009 | Brumfield |
| 7,744,598 B2 | 6/2010 | Brumfield |
| 8,425,515 B2 | 4/2013 | Gamache |
| 8,425,520 B2 | 4/2013 | Zalenski |
| 8,470,003 B2 | 6/2013 | Voellmicke |
| 2002/0017472 A1 | 2/2002 | Weisshaupt |
| 2002/0029039 A1 | 3/2002 | Zucherman |
| 2002/0046961 A1 | 4/2002 | Levinson |
| 2002/0120335 A1 | 8/2002 | Angelucci |
| 2002/0128682 A1 | 9/2002 | Prestel |
| 2003/0045935 A1 | 3/2003 | Angelucci |
| 2003/0045936 A1 | 3/2003 | Angelucci |
| 2003/0125738 A1 | 7/2003 | Khanna |
| 2004/0030388 A1 | 2/2004 | Null |
| 2004/0102775 A1 | 5/2004 | Huebner |
| 2004/0106927 A1 | 6/2004 | Ruffner |
| 2004/0162558 A1 | 8/2004 | Hegde |
| 2004/0210222 A1 | 10/2004 | Angelucci |
| 2005/0038436 A1 | 2/2005 | Michelson |
| 2005/0085818 A1 | 4/2005 | Huebner |
| 2005/0107877 A1 | 5/2005 | Blain |
| 2005/0119657 A1 | 6/2005 | Goldsmith |
| 2005/0131412 A1 | 6/2005 | Olevsky |
| 2005/0149021 A1 | 7/2005 | Tozzi |
| 2005/0182407 A1 | 8/2005 | Dalton |
| 2005/0234765 A1 | 10/2005 | Blumberg |
| 2005/0251138 A1 | 11/2005 | Boris |
| 2005/0273100 A1 | 12/2005 | Taylor |
| 2006/0064091 A1 | 3/2006 | Ludwig |
| 2006/0079931 A1 | 4/2006 | Brennan |
| 2006/0190033 A1 | 8/2006 | Molloy |
| 2006/0247635 A1 | 11/2006 | Gordon |
| 2007/0123869 A1 | 5/2007 | Chin |
| 2007/0219582 A1 | 9/2007 | Brunelle |
| 2007/0276376 A1 | 11/2007 | Link |
| 2008/0009865 A1 | 1/2008 | Taylor |
| 2008/0183217 A1 | 7/2008 | Glaser |
| 2008/0215096 A1 | 9/2008 | Nash |
| 2008/0302688 A1 | 12/2008 | Laconi-Forrer |
| 2010/0016900 A1 | 1/2010 | Terres |
| 2010/0057127 A1 | 3/2010 | McGuire |
| 2010/0094351 A1* | 4/2010 | Haggenmaker .... A61B 17/7044 606/286 |
| 2011/0106083 A1 | 5/2011 | Voellmicke |
| 2011/0106084 A1 | 5/2011 | Gamache |
| 2011/0106087 A1 | 5/2011 | Gamache |
| 2011/0106169 A1 | 5/2011 | Zalenski |
| 2012/0271359 A1* | 10/2012 | Stevenson .......... A61B 17/7071 606/281 |
| 2013/0060283 A1 | 3/2013 | Suh et al. |

FOREIGN PATENT DOCUMENTS

| | | |
|---|---|---|
| WO | WO 1995012356 | 5/1995 |
| WO | WO 1996005778 | 2/1996 |
| WO | WO 1997009940 | 3/1997 |
| WO | WO 1999037221 | 7/1999 |
| WO | WO 2000044290 | 8/2000 |
| WO | WO 2003007826 | 1/2003 |
| WO | WO 2003020142 | 3/2003 |
| WO | WO 2003101319 | 12/2003 |
| WO | WO 2005096969 | 10/2005 |
| WO | WO 2005041752 | 5/2006 |
| WO | WO 2006104487 | 10/2006 |
| WO | WO 2007127918 | 11/2007 |
| WO | WO 2011040983 | 4/2011 |

OTHER PUBLICATIONS

Frank, A Technique for Cervial Laminoplasty Using Mini Plates, British Journal of Neurosurgery, 1994, vol. 8, pp. 197-199.

(56) References Cited

OTHER PUBLICATIONS

Stanescue, "Morphometic Evaluation of the Cervico-Thoracic Junction, Practical Consideratoins for Posterior Fixation of the Spine", Spine, vol. 19, No. 18, 1994, pp. 2082-2088, J.B. Lippincott Co.

\* cited by examiner

LAMINOPLASTY PLATES AND METHODS OF EXPANDING THE SPINAL CANAL

This application is a continuation of U.S. patent application Ser. No. 14/986,780 filed Jan. 4, 2016 and issued on Oct. 24, 2017 as U.S. Pat. No. 9,795,420, which is a continuation of U.S. patent application Ser. No. 13/905,643 filed May 30, 2013, now abandoned, which is a divisional of U.S. application Ser. No. 12/609,251 filed Oct. 30, 2009 and issued on Jun. 25, 2013 as U.S. Pat. No. 8,470,003, the disclosures of all of which are hereby incorporated by reference as if set forth in their entirety herein.

CROSS-REFERENCE TO RELATED APPLICATIONS

This application is a divisional application of U.S. patent application Ser. No. 12/609,251, filed on Oct. 30, 2009, which is hereby incorporated herein by reference.

BACKGROUND

The spinal cord can become compressed due to a variety of pathological conditions, thereby causing myelopathy and subsequent pain, weakness, or paralysis. One way to alleviate spinal cord compression is to expand the spinal canal, typically by displacing bone, such as the lamina, that surrounds the spinal cord. This procedure, generally referred to as laminoplasty, typically involves making two types of cuts into the lamina, a complete osteotomy through the lamina on one side of the spine and a partial osteotomy, or "green stick", on the contra-lateral lamina, which preserves the bottom cortex and creates a flexible hinge in the bone. This bridge of bone is then levered open about the hinge and fixed with bone graft, plates, and screws. Screws are often driven into this somewhat unstable mass of bone, which could pose a risk of injury to the spinal cord or an opportunity to fracture the green stick cut.

SUMMARY

Disclosed herein are improved laminoplasty plates and methods of expanding the spinal canal to decompress the spinal cord.

In one aspect, a method of expanding the spinal canal of a vertebra may include inserting a bone anchor into a first lamina of the vertebra, cutting completely through the first lamina to create a space in the first lamina, cutting partially through a second, contra-lateral lamina of the vertebra to create a partial cut in the second lamina, engaging a first segment of a plate with the bone anchor, pivoting the bone anchor and the first lamina about the partial cut in the second lamina to increase the extent of the space in the first lamina, and connecting a second segment of the plate to a portion of the vertebra across the space from the first segment of the plate such that the plate spans the space and stabilizes the vertebra.

In another aspect, a laminoplasty plate may include a first plate segment including a pair of spaced apart arms defining a slot that opens at a first end of the plate, a second plate segment including a first hole for receiving a bone anchor, a central longitudinal axis of the plate extending from the first segment of the plate to the second segment of the plate, and a central plate segment interposed between the first plate segment and the second plate segment. The first plate segment and the second plate segment may lie in separate approximately parallel planes and the central plate segment may connect the first plate segment and the second plate segment and may lie in a plane that intersects the parallel planes.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the devices and methods disclosed herein and, although not to scale, show relative dimensions.

DETAIL DESCRIPTION OF EXEMPLARY EMBODIMENTS

Figure 1:
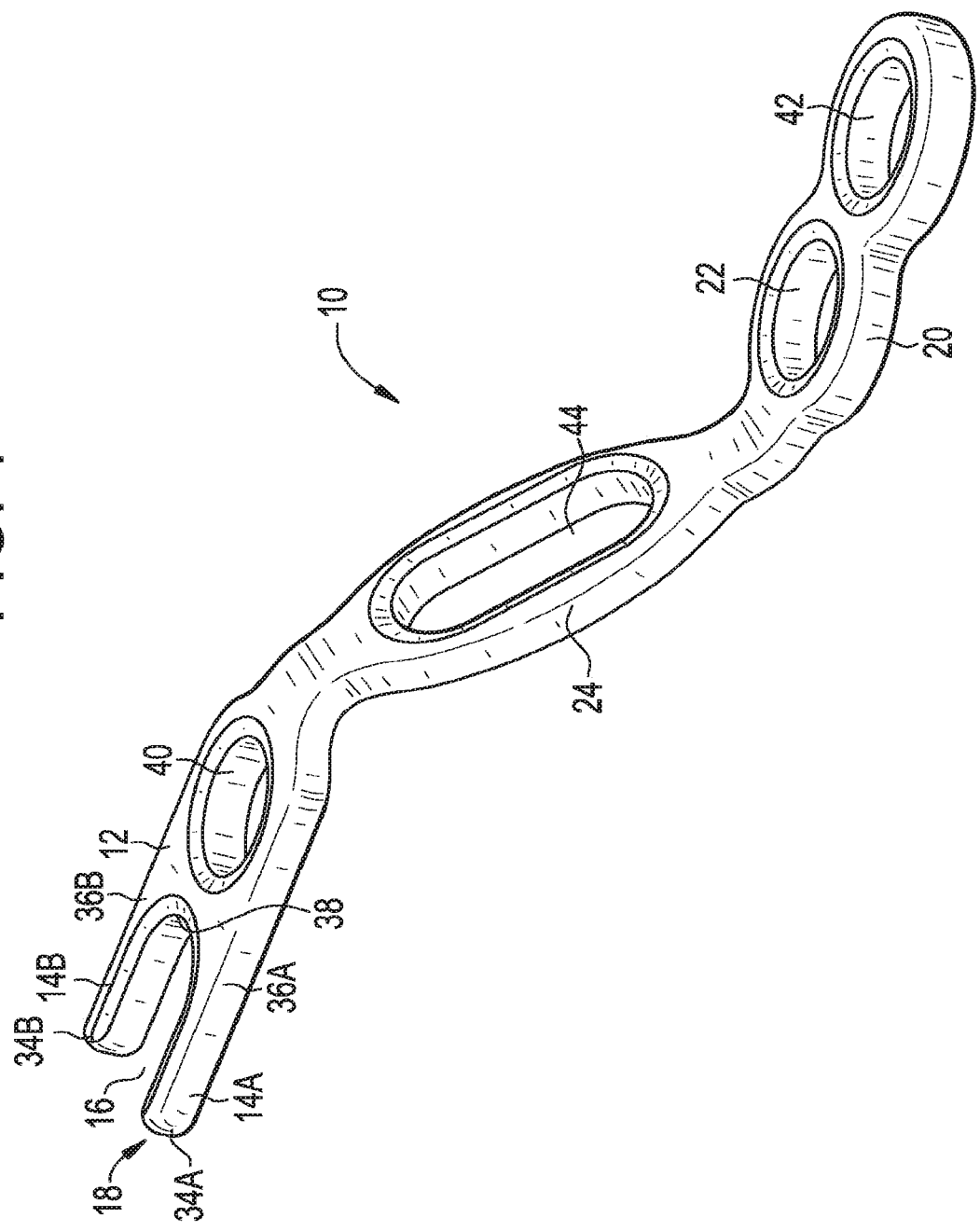
FIG. 1 is a perspective view of an exemplary embodiment of a laminoplasty plate.
Figure 2:
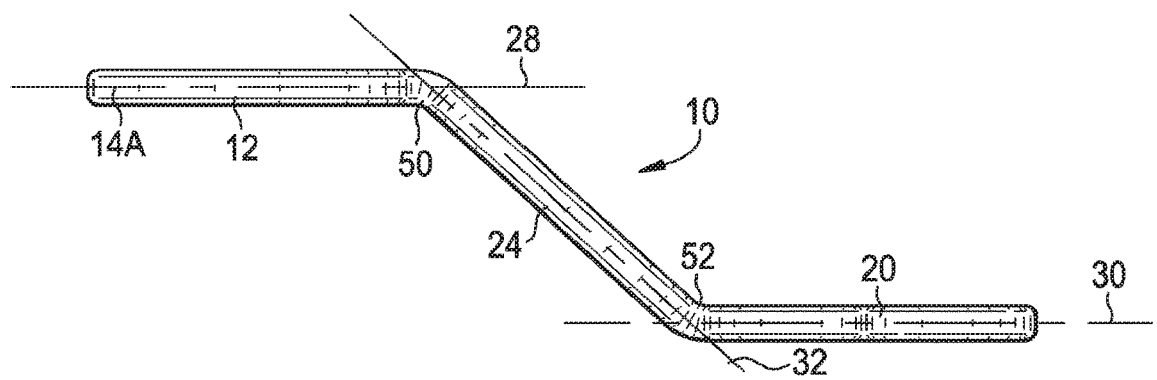
FIG. 2 is a side view of the laminoplasty plate of FIG. 1.
Figure 3:
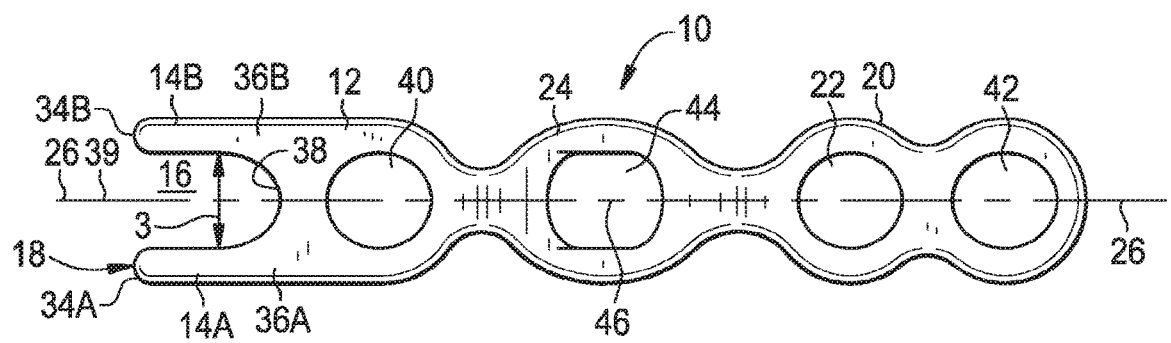
FIG. 3 is a top view of the laminoplasty plate of FIG. 1.
Figure 4:
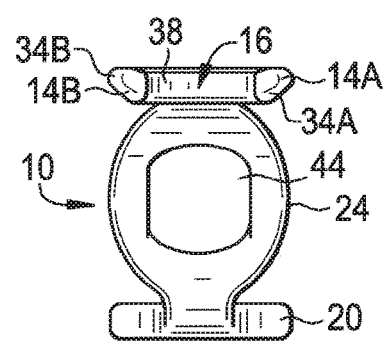
FIG. 4 is a front view of the laminoplasty plate of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-4 illustrate an exemplary embodiment of a laminoplasty plate 10. The exemplary laminoplasty plate includes a first plate segment 12 including a pair of spaced apart arms 14A, 14B defining a slot 16 that opens at a first end 18 of the plate 10. The exemplary plate 10 further includes a second plate segment 20 including at least one hole, e.g., first hole 22, for receiving a bone anchor and a central plate segment 24 interposed between the first plate segment 12 and the second plate segment 20. A central longitudinal axis 26 of the plate 10 extends from the first plate segment 12 to the second plate segment 20. The first plate segment 12 and the second plate segment 20, in the exemplary embodiment lie in separate, approximately parallel planes, e.g., first plane 28 and second plane 30, respectively, and the central plate segment 24 connects the first plate segment 12 and the second plate segment 20 and lies in a plane, e.g., third plane 32 that intersects the parallel planes.

Continuing to refer to FIGS. 1-4, the first plate segment 12 is configured to permit the first plate segment 12 to engage a previously implanted bone anchor, as described in more detail below. In particular, the slot 16 is open at the first end 18 of the plate 10 such that the arms 14A, 14B may be positioned about the bone anchor, by, for example, sliding the arms 14A, 14B about the bone anchor thereby positioning at least a portion of the bone anchor within the slot 16. In the exemplary embodiment, the distance W between the arms 14A, 14B, e.g., the width of the slot 16, is greater than the diameter of the shank of the bone anchor. Each arm 14A, 14B, has a free end 34A, 3413 and a fixed end 36A, 36B which are connected to the first plate segment 12. An interconnecting surface 38 connects the fixed ends 36A, 36B of the arms 14A, 14B and defines the base of the slot 16. In the exemplary embodiment, the interconnecting surface 38 is arcuate in shape providing the slot 16 with a generally U-shape.

Figure 11:
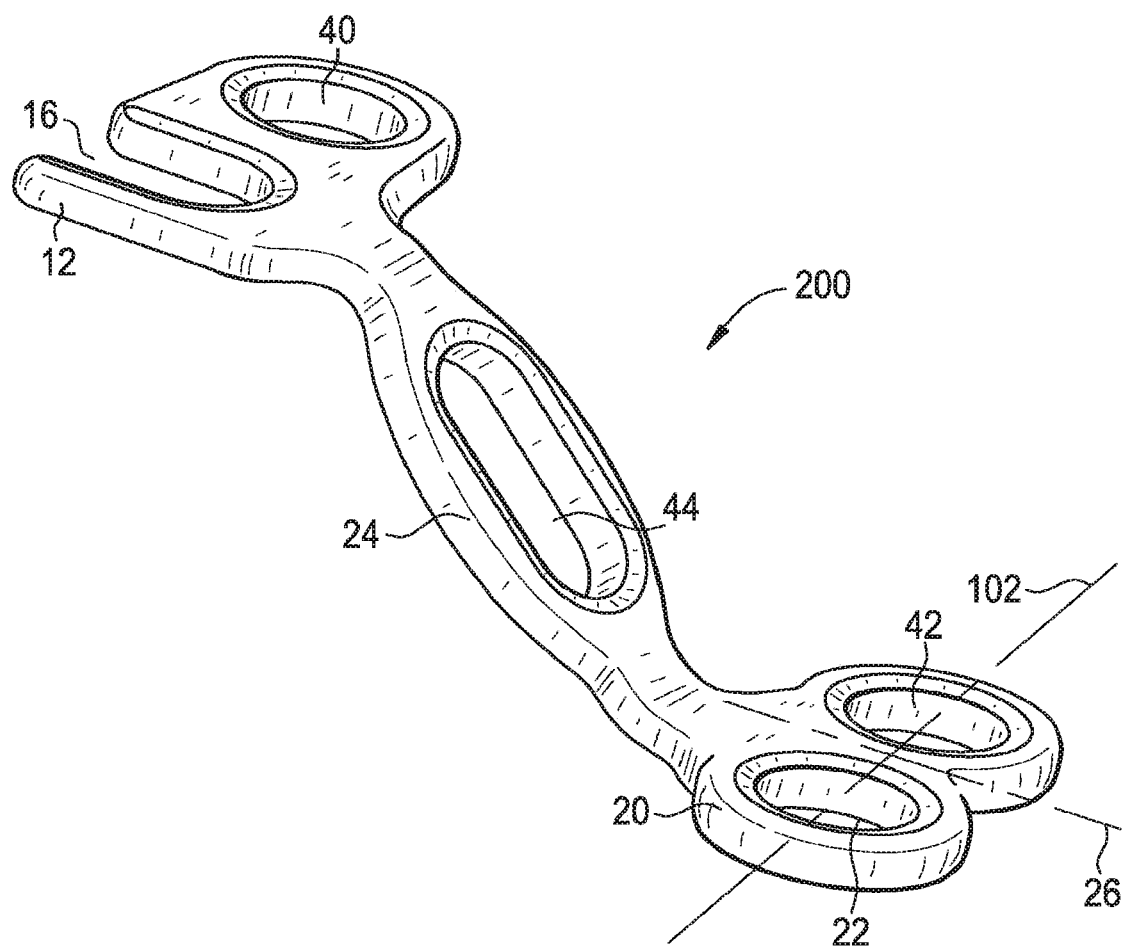
FIG. 11 is a perspective view of another exemplary embodiment of a laminoplasty plate.

The slot 16 may have a central slot axis 39 extending from the first end 18 to the interconnecting surface 38. In the exemplary embodiment, the central slot axis 18 is coincident with the central longitudinal axis 26. The first plate segment 12 may include one or more additional holes 40 for receiving a bone anchor. The additional hole 40 or holes may be aligned along the central longitudinal axis 26 of the plate 10, such that, for example, the center of the hole 40 is positioned on central longitudinal axis 26, as in the exemplary embodiment. Alternatively, one or more of the holes 40 may be offset from the central longitudinal axis 26. For example, in the exemplary embodiment of a laminoplasty plate 200 illustrated in FIG. 11, the hole 40 is positioned offset from the central longitudinal axis 26 and the hole 40 and slot 16 may be aligned along an axis that is generally transverse to the central longitudinal axis 26. The hole 40 may have a generally circular cross section, as in the exemplary embodiment, or, alternatively, may have other suitable shapes. For example, the hole 40 may be in the form of elongated, closed slot having an elliptical cross section.

Figure 5:
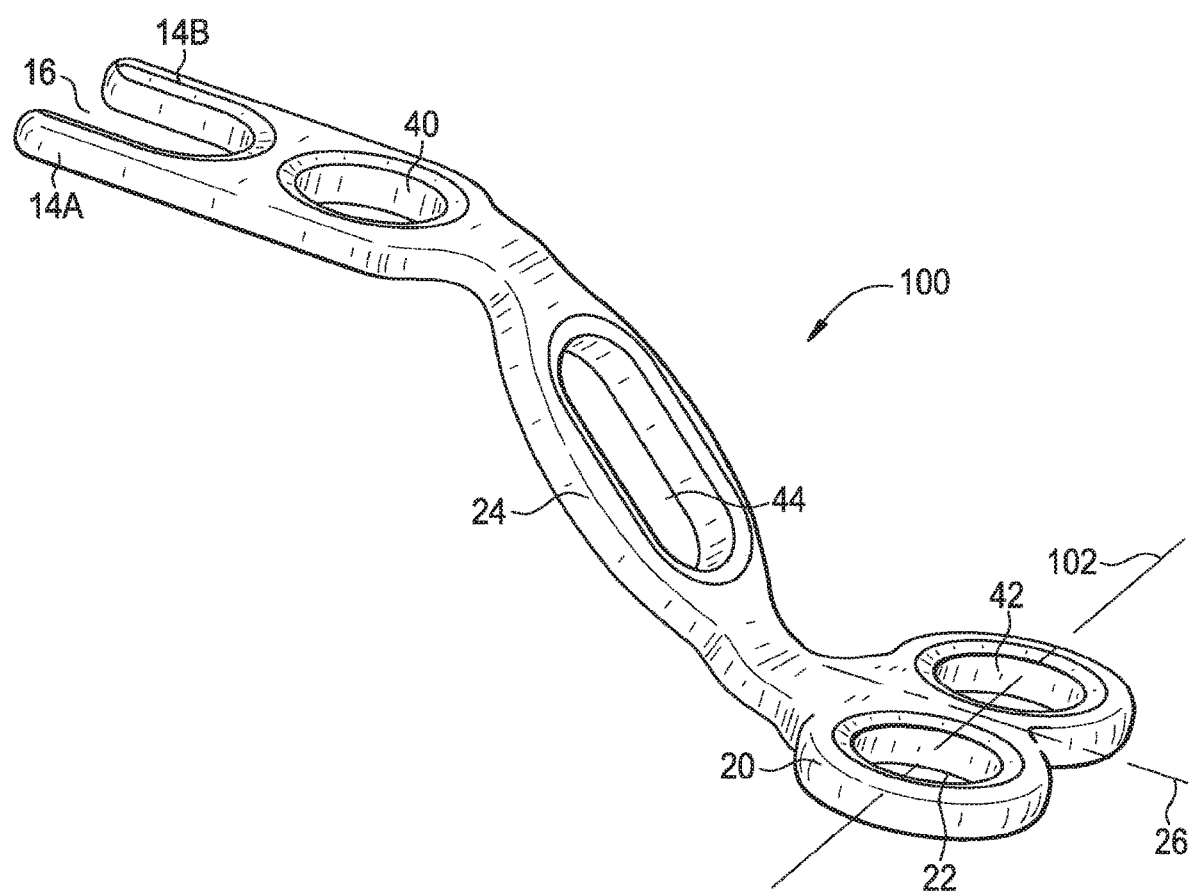
FIG. 5 is a perspective view of another exemplary embodiment of a laminoplasty plate.

The second plate segment 20 may include one or more additional holes 42 for receiving a bone anchor. The first hole 22 and the additional hole 42 or holes may be aligned along the central longitudinal axis 26 of the plate 10, such that, for example, the center of the first hole 22 and the additional hole 42 is positioned on central longitudinal axis 26, as in the exemplary embodiment. Alternatively, one or more of the holes 42 may be offset from the central longitudinal axis 26. For example, in an alternative exemplary embodiment of a laminoplasty plate 100 illustrated in FIG. 5 and the alternative exemplary embodiment of a laminoplasty plate 200 illustrated in FIG. 11, the first hole 22 and the additional hole 42 are aligned along an axis 102 that is generally transverse to the central longitudinal axis 26.

The first hole 22 and the additional hole 42 each may have a generally circular cross section, as in the exemplary embodiment, or, alternatively, may have other suitable shapes. For example, the first hole 22 and the additional hole 42 may be in the form of elongated, closed slot having an elliptical cross section. Such a configuration may allow the plate 10 to be adjusted relative to the bone anchor positioned in the first hole 22 and the additional hole 42 along the longitudinal axis of the closed slots defining the first and additional holes.

The central plate segment 24 may include an opening for receiving an anchor to connect a bone graft to the plate 10. In the exemplary embodiment, the opening is an elongated, closed graft slot 44 having a generally elliptical shape. The graft slot 44 has a central slot axis 46 that, in the exemplary embodiment, is coincident with the central longitudinal axis 26 of the plate 10. The shape of the graft slot 44 can vary. For example, the graft slot 44 may be circular in shape. Moreover, multiple, spaced-apart graft slots 44 may be provided rather than a single elongated slot.

The junction 50 between the first plate segment 12 and the central plate segment 24 and the junction 52 between the second plate segment 20 and the central plate segment 24 may be constructed to permit bending of the first plate segment 50 at the junction 50 relative to the central plate segment 24 and bending of the second plate segment 20 at the junction 52 relative to the central plate segment 24. To permit such bending, the junction 50 and the junction 52 may have a reduced thickness compared to other segments of the plate 10.

The plate 10 may be constructed of any biocompatible material suitable for implantation within the human body, including, for example, stainless steel, titanium and titanium alloys, and polymers, including biodegradable polymers.

Referring to FIGS. 6-10, an exemplary method of expanding the spinal canal of a vertebra 70. The vertebra 70 to be treated, in the exemplary method, is a cervical vertebra, although the methods and plates described herein may be used in vertebra throughout the spine. The exemplary vertebra 70 includes a first lamina 72, first lateral mass 76, a second, contra-lateral lamina 74, a second, contra-lateral lateral mass 78, and a spinous process 80 between the first lamina 72 and the second lamina 74. A bulging portion of the disc 80 has entered the spinal canal 82 of the vertebra 70 and is impinging on the spinal cord 84. The exemplary method will expand the spinal canal 82 such that the bulging disc 80 no longer impinges the spinal cord 84.

The exemplary method includes inserting a first bone anchor 60A into the first lamina 72 of the vertebra 70. The exemplary bone anchor 60A includes a proximal head 62 and a distal bone engaging shaft 64. The proximal head 62 may have an increase diameter compared to the shaft 64 and may include a drive feature to facilitate connection of an instrument, such as a screwdriver, to the bone anchor 60A. The distal bone engaging shaft 64 may have a thread for engaging bone. In the exemplary method, the bone anchor 60A is inserted into the intact first lamina 74, i.e., prior to cutting the first lamina 74. a result, the first lamina 74 is stable during the process of inserting the first bone anchor 60A. Alternatively, the bone anchor may be inserted into the vertebra after the cutting the first lamina 74 and prior to the making the partial cut in the contra-lateral lamina.

Figure 6:
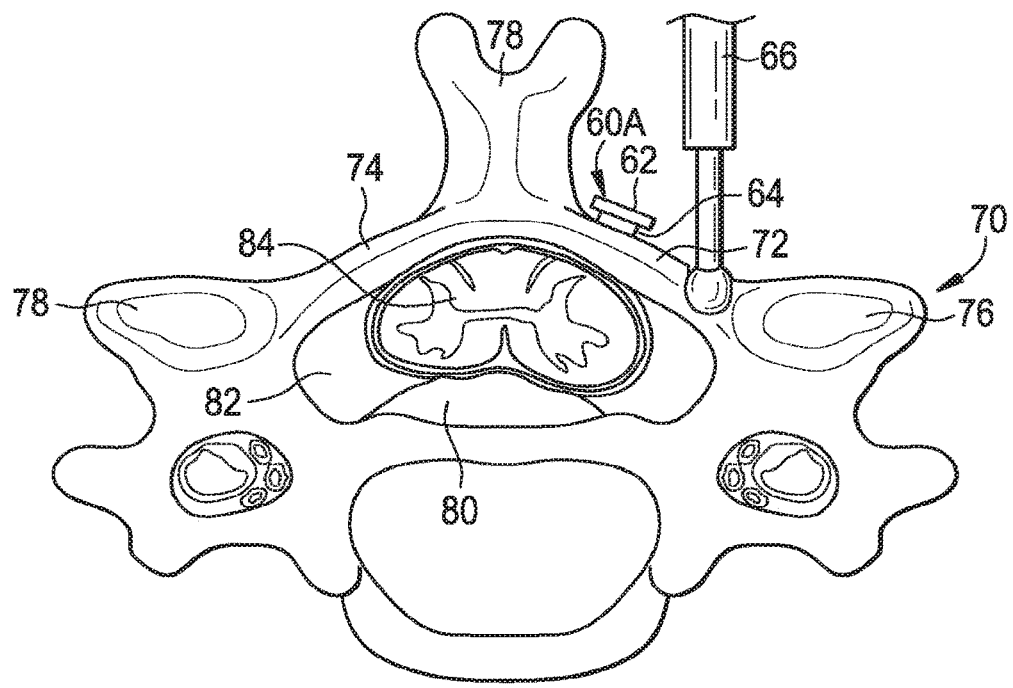
FIG. 6 is a side view in cross section of a vertebra, illustrating creating a cut through a first lamina of the vertebra.
Figure 7:
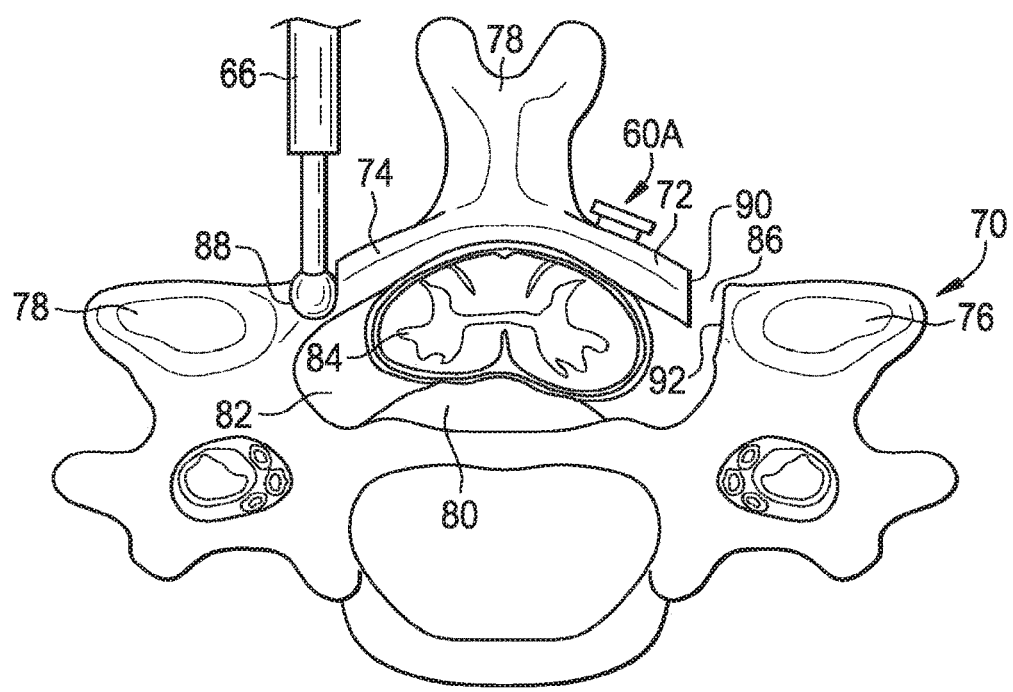
FIG. 7 is a side view in cross section of the vertebra of FIG. 6, illustrating creating a partial cut through the second, contra-lateral lamina of the vertebra.

Once the first bone anchor 60A is inserted, the first lamina 74 is cut completely through to create a space 86 in the first lamina 72, as illustrated in FIGS. 6 and 7. An instrument, such as a bur 66 or any other bone cutting instrument, may be used to cut the first lamina 72. The cut and, thus, the subsequent space 86 may be made at the junction of the first lamina 72 and the first lateral mass 76, as illustrated in FIG. 6.

The second, contra-lateral lamina 76 of the vertebra 70 may be partially cut to create a partial cut 88 in the second lamina 76. An instrument, such as a bur 66 or any other bone cutting instrument, may be used to partially cut the second lamina 74. The partial cut 88, and the subsequent hinge created by the partial cut 88 as discussed below, may be made at the junction of the second lamina 74 and the second lateral mass 78, as illustrated in FIG. 7. The amount of bone removed during the partially cutting is preferably sufficient to create a green-stick fracture and the deep cortex is preferably preserved to prevent a complete fracture of the second lamina 74.

After creation of the partial cut 88, the first lamina 72 may be pivoted about the partial cut 88 in the second lamina 76 with the partial cut 88 acting as a hinge. The effect of this pivoting operation is to increase the extent of the space 86 in the first lamina 72, e.g., the distance between the first cut edge 90 and the second cut edge 92, and to expand the spinal canal 82, thereby decompressing the spinal cord 84. The pivoting of the first lamina 72 may be accomplished by grasping in the first bone anchor 60A and using the first bone anchor 60A to pivot the first lamina 72. An instrument, such as a forceps or the like, may be used to grasp the first bone anchor 60A. Once the instrument grasps the bone anchor 60A, the instrument may be manipulated to pivot the first bone anchor and, thus, the first lamina 72. Alternatively, the surgeon may grasp the bone anchor 60A with his hand to pivot the first lamina 72.

A laminoplasty plate may be attached to the first vertebra 70 to stabilize the first lamina 72 relative to the first lateral mass 76 after expansion of the spinal canal 82. The laminoplasty plate may bridge the space 86 by connecting at one end to the first lamina 72 and at another end to the lateral mass 76. The laminoplasty plate may be connected to the first lamina 72 and the first lateral mass 76 by bone anchors. Although the method described below will describe the use of the exemplary laminoplasty plate 10, other laminoplasty plates, including exemplary laminoplasty plate 100, may be utilized to stabilize the vertebra 70.

In one exemplary method, a laminoplasty plate, such as laminoplasty plate 10 described above, may be connected to the vertebra 70 prior to pivoting of the first lamina 72. For example, the first segment 12 of the plate 10 may be engaged with the first bone anchor 60A prior to pivoting the first lamina 72 to expand the spinal canal 82. The first portion 12 of the plate 10 may be engaged to the first bone anchor 60A by sliding the arms 14A, 14B about the distal shaft 64 of the bone anchor 60A to position the bone anchor 60A within the slot 16. Once the bone anchor 60A is positioned within the slot 16, the bone anchor 60A may be advanced further into the first lamina 72 to compress the proximal head 62 of the bone anchor 60A against the top surface of the plate 10. This final tightening of the first bone anchor 60A may occur before or after the connection of the second plate segment 20 to the vertebra 70.

Once the first segment 12 of the plate 10 is connected to the first lamina 72, the plate 10 may be manipulated to cause the first bone anchor 60 and the first lamina 72 to pivot about the partial cut 88. The plate 10 may be manipulated by hand by the surgeon or may be manipulated by an instrument, such as, for example, a forceps, plate holder, or the like. An exemplary plate holder is described in commonly owned, co-pending US Patent Application Publication No. US 2011/0106087 A1, entitled "Bone Plate Holder" concurrently filed herewith, which is incorporated herein by reference.

In alternative methods, the laminoplasty plate may be connected to vertebra 70, by, for example, engaging the plate 10 to the first bone anchor 60, after the first lamina 72 has been pivoted to expand the spinal canal.

Figure 9:
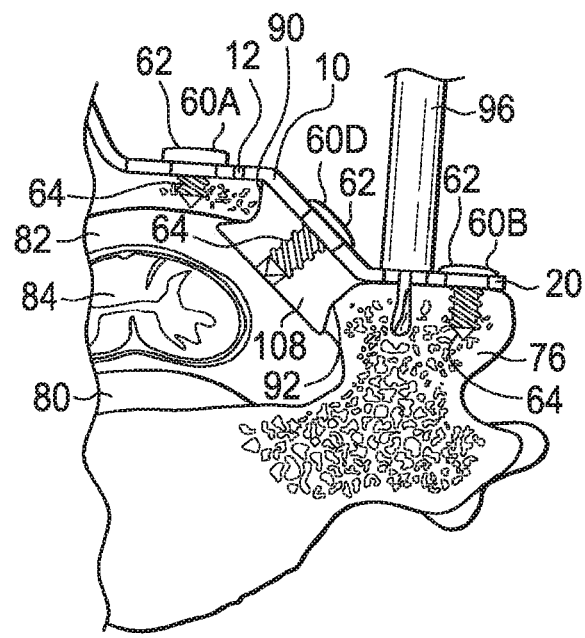
FIG. 9 is a partial side view in cross section of the vertebra of FIG. 6, illustrating connecting the laminoplasty plate and bone graft of FIG. 8 to the vertebra.

The second segment 20 of the plate 10 may be connected to a portion of the vertebra 70 across the space from the first segment 12 of the plate 10 such that the plate 10 spans the space 86 and stabilizes the vertebra 70. For example, the second segment 20 of the plate 10 may be connected to the first lateral mass 76, as illustrated in FIG. 9. The second segment 20 may be connected to the first lateral mass 76 by inserting bone anchors, for example, bone anchor 60B, through hole 22 and through hole 42 of the second plate segment 20 and into the first lateral mass 76. A drill 96 may be used to provide a hole within the first lateral mass 76 for receiving a bone anchor.

A second bone anchor, e.g., a bone anchor 60C, may be inserted through hole 40 and into the first lamina 72 to further secure the first plate segment 12 to the first lamina 72. The second bone anchor 60C may be inserted through the first plate segment 12 and into the first lamina 72 after the first lamina 72 is pivoted about the partial cut 88 or after the second plate segment 20 is connected to the vertebra. Alternatively, the second bone anchor 60C may be inserted through the first plate segment 12 and into the first lamina 72 before the first lamina 72 is pivoted about the partial cut 88.

Figure 8:
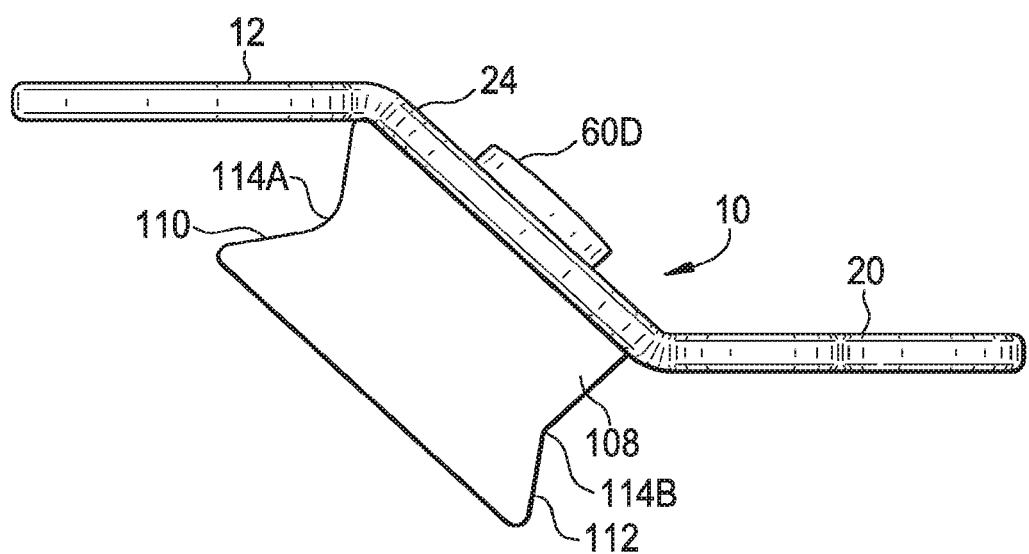
FIG. 8 is a side view of the plate of FIG. 1, illustrating a bone graft connected to the plate.

In certain embodiments, a bone graft 108 may be positioned within the expanded space 86 to facilitate fusion of the first lamina 72 across the space 86. The bone graft 108 may be allograft or autograft and may be connected to the laminoplasty plate prior to positioning within the space 86. For example, the bone graft 108 may be connected to the central segment 42 of the laminoplasty plate 10 or the central segment 24 of the laminoplasty plate 100 with a bone anchor, e.g. bone anchor 60D, positioned through graft slot 44 and into the bone graft 108, as illustrated in FIG. 8. The bone graft 108 may have a first end 110 and a second end 112 configured to engage the first cut edge 90 and the second cut edge 92. In the exemplary embodiment, for example, the first end 110 and the second end 112 each include a notch 114A, 114b into which a respective one of the first cut edge 90 and the second cut edge 92 may be seated.

The bone graft 108 may be connected to the laminoplasty plate using an instrument that holds the bone graft 108 relative to the plate during insertion of the bone anchor 601). An exemplary instrument is described in commonly owned, co-pending US Patent Application Publication No. US 2011/0106084 A1, entitled "Bone Graft Loading instruments and Methods of Connecting a Bone Graft to a Bone Plate" concurrently filed herewith, which is incorporated herein by reference.

FIG. 9 illustrates exemplary laminoplasty plate 10 connected to a bone graft 108 and the bone graft 108 positioned in the expanded space 86. The spinal canal 82 of the vertebra 70 is expanded to decompress the spinal cord 84 and the laminoplasty plate 10 stabilizes the expanded vertebra 70.

Figure 10:
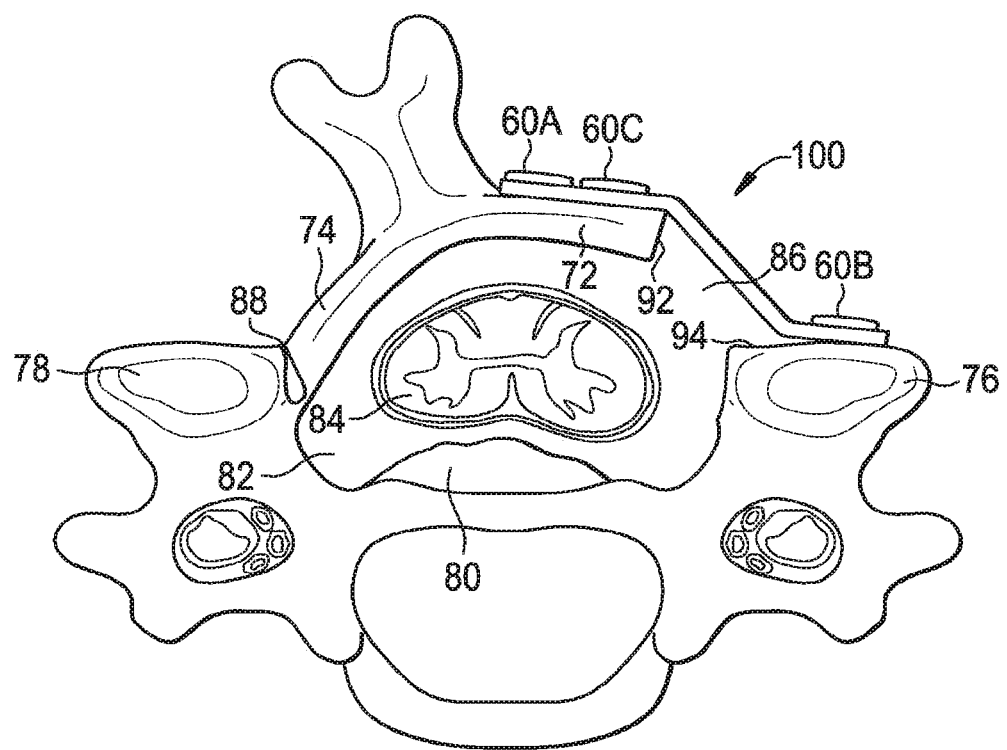
FIG. 10 is a side view in cross section of a vertebra, illustrating the laminoplasty plate of FIG. 5 connected to the vertebra.

In certain exemplary embodiments, the method of expanding the spinal canal of a vertebra may be completed without a bone graft. In such cases, the laminoplasty plate may be connected to the vertebra without the bone graft. For example, FIG. 10 illustrates exemplary laminoplasty plate 100 connected to the first lamina 72 and the first lateral mass 76 and spanning the expanded space 86. The spinal canal 82 of the vertebra 70 is expanded to decompress the spinal cord 84 and the laminoplasty plate 100 stabilizes the expanded vertebra 70.

The exemplary method may be used to treat multiple vertebrae in a single procedure. For example, the spinal canal of two or more adjacent vertebra may be expanded and laminoplasty plates may be engaged to each vertebra using the methods described above.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A laminoplasty system comprising:
    a plate including:
        a first plate segment including
            a pair of spaced apart arms defining a slot that opens at a first end of the plate, the pair of spaced apart arms being sized and configured to permit the first plate segment to slidably engage a bone anchor;
        a second plate segment defining
            a first hole being sized and configured to receive a bone anchor and a second hole being sized and configured to receive a bone anchor;
        a third plate segment interposed between the first plate segment and the second plate segment, the third plate segment defining an opening;
        wherein the first plate segment and the second plate segment are disposed in separate approximately parallel planes and the third plate segment connects the first plate segment and the second plate segment and is disposed in a plane that intersects the approximately parallel planes;
        wherein the plate includes a central longitudinal axis extending along the first plate segment, second plate segment, and third plate segment; and wherein the slot, the first hole, and the second hole are disposed on the central longitudinal axis; and
        wherein the first plate segment defines a third hole being sized and configured to receive a bone anchor.

2. The laminoplasty system of claim 1, wherein the slot is sized and configured to permit the first plate segment to slidably engage a bone anchor implanted in a portion of a lamina for securement of the first plate segment to the lamina by the bone anchor.

3. The laminoplasty system of claim 1, wherein the opening of the third plate segment is sized and configured to receive a graft anchor.

4. The laminoplasty system of claim 3, further comprising a graft anchor disposed in the opening of the third plate segment and a bone graft secured to the graft anchor.

5. The laminoplasty system of claim 3, wherein the opening of the third plate segment is an elongated slot having a slot axis coincident with the central longitudinal axis.

6. The laminoplasty system of claim 1, wherein the third hole is disposed on the central longitudinal axis.

7. The laminoplasty system of claim 6, further comprising a first bone anchor disposed in the first hole, a second bone anchor disposed in the second hole, and a third bone anchor disposed in the third hole.

8. The laminoplasty system of claim 1, wherein the first plate segment meets the third plate segment at a first junction and the thickness of plate at the first junction is less than the thickness of the plate at the first plate segment whereby the first junction is bendable.

9. The laminoplasty system of claim 8, wherein the second plate segment meets the third plate segment at a second junction and the thickness of plate at the second junction is less than the thickness of the plate at the second plate segment whereby the second junction is bendable.

10. The laminoplasty system of claim 1, wherein the shape of the first hole is different than the shape of the opening.

11. The laminoplasty system of claim 1, wherein the slot is U-shaped.

\* \* \* \* \*